US00PP12611P2

(12) United States Plant Patent
Jacobsen

(10) Patent No.: US PP12,611 P2
(45) Date of Patent: May 7, 2002

(54) POINSETTIA PLANT NAMED 'JACABIA'

(75) Inventor: Aase Jacobsen, Skibby (DK)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/432,715

(22) Filed: Nov. 2, 1999

(51) Int. Cl.[7] ..... A01H 5/00
(52) U.S. Cl. ..... Plt./307

(58) Field of Search ..... Plt./307

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Poinsettia plant named 'Jacabia', characterized by its unique narrowly ovate red-colored bracts that are held somewhat upright; unique narrowly ovate dark green leaves; compact plant habit; late flowering, response time about 10 weeks; and excellent postproduction longevity.

2 Drawing Sheets

BACKGROUND OF THE INVENTION

The present invention relates to a new and distinct cultivar of Poinsettia plant, botanically known as *Euphorbia pulcherrima* Willd., and hereinafter referred to by the name 'Jacabia'.

The new Poinsettia is a product of a mutation induction breeding program conducted in Skibby, Denmark. The objective of the program is to create new Poinsettia cultivars having interesting bract and leaf display, desirable bract and foliage color and form, strong and freely branching stems and good post-production longevity.

The new Poinsettia originated by exposign unrooted cuttings of the commercial *Euphorbia pulcherrima* Willd. cultivar 490, disclosed in U.S. Plant Pat. No. 7,825, to gamma-ray radiation. The new Poinsettia was discovered and selected in December, 1995 in Encinitas, Calif. The selection of this plant was based on its unique bract shape.

Asexual reproduction of the new Poinsettia by terminal cuttings taken at Encinitas, Calif., has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Jacabia'. These characteristics in combination distinguish 'Jacabia' as a new and distinct cultivar:

1. Unique narrowly ovate red-colored bracts that are held somewhat upright.
2. Unique narrowly ovate dark green leaves.
3. Compact plant habit and short internodes.
4. Late flowering, response time about 10 weeks.
5. Excellent postproduction longevity.

In side-by-side comparisons conducted in Encinitas, Calif., plants of the new Poinsettia differed from plants of the parent cultivar, 490, in the following characteristics:

1. Plants of the new Poinsettia are shorter, more compact and less vigorous than plants of '490'.
2. Plants of the new Poinsettia are not as freely branching as plans of '490'.

3. Leaves of the new Poinsettia are smaller, narrower, more acuminate and lighter green than leaves of '490'.
4. Petioles of the new Poinsettia are shorter than petioles of '490'.
5. Plants of the new Poinsettia have much smaller inflorescences than plants of '490'.
6. Bracts of the new Poinsettia are more upright, smaller, narrower and more acuminate than bracts of '490'.
7. Bract color of the new Poinsettia is more crimson than bract color '490'.
8. Plants of the new Poinsettia flower about 10 to 14 days later than plants of '490'.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type.

The photograph at the top of the first sheet comprises a side perspective view of a typical plant of 'Jacabia'.

The photograph at the bottom of the first sheet comprises a top perspective view of a typical plant of 'Jacabia'.

The photograph on the second sheet is a close-up view of typical bracts and leaves of 'Jacabia' (left) and '490' (right). Bract and foliage colors in the photographs may differ from actual colors due to light reflectance.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The following observations and measurements describe plants grown in Encinitas, Calif., under commercial practive in a glass-covered greenhouse with day temperatures ranging from 21 to 27° C., night temperatures ranging from 18 to 20° C., and light levels about 4,000 foot-candles. Plants were grown in 16-cm pots, pinched one time, and flowered under naturally lengthening nyctoperiods during the fall/early winter.

In the following description, color references are made to The Royal Horticultural Society Colour Chart except where general terms of ordinary dictionary significance are used.

Botanical classification: *Euphorbia pulcherrima* Willd. 'Jacabia'.

Parentage: Induced mutation of *Euphorbia pulcherrima* Willd. cultivar 490, disclosed in U.S. Plant Pat. No. 7,825.

Propagation:

*Type cutting*.—Terminal cuttings.

*Time to initiate roots*.—Summer: About 7 days at 24° C. Winter: About 10 days at 22° C.

*Time to develop roots*.—Summer: About 26 days at 24° C. Winter: About 26 days at 22° C.

*Rooting habit*.—Thick, freely branching, becoming fibrous with development.

Plant description:

*Plant form*.—Inverted triangle; rounded canopy.

*Growth habit*.—Short, compact, with short internodes. Branching is enhanced by removing the shoot apex. Low vigor.

*Plant height*.—About 17 cm.

*Crop time*.—From unrooted cuttings to a flowering plant in a 16.5-cm container, about 18 weeks are required.

*Stem description*.—Number of lateral branches: About five lateral branches are formed after removal of the terminal apex. Lateral branch length: About 10.5 cm. Internode length: About 1 cm. Stem color: 146A with anthocyanin overtones, 59B.

*Foliage description*.—Quantity of leaves per lateral branch: About 6. Length: About 10.25 cm. Width: About 4.75 cm. Shape: Narrowly ovate with pointed lobes. Apex: Elongated acuminate. Base: Rounded acute. Margin: Entire. Texture: Smooth, but slightly rugose. Mostly glabrous with very slight pubescence on lower surface. Color: Young foliage, upper surface: 146A. Young foliage, lower surface: 146B to 146C. Mature foliage, upper surface: 147A. Mature foliage, lower surface: 147B. Venation, upper surface: 146C. Venation, lower surface: 147D. Petiole: Length: About 2.8 cm. Diameter: About 2 mm. Color: 59A to 59B.

Inflorescence description:

*Inflorescence type and habit*.—Inflorescences are compound corymbs of cyathia with colored flower bracts subtending the cyathia.

*Natural flowering season*.—Autumn/winter in Northern Hemisphere. Flower initiation and development can be induced under long nyctoperiod conditions. Late flowering, response time is about 10 weeks.

*Quantity of inflorescences*.—One per lateral branch, usually about five per plant.

*Inflorescence size*.—Diameter: About 22 cm. Height (depth): About 4 cm.

*Flower bracts*.—Quantity of flower bracts per inflorescence: Usually about 7 outer primary bracts, 5 secondary bracts, and about 6 smaller upright tertiary bracts per inflorescence. Length, largest bracts: About 11.5 cm. Width, largest bracts: About 5 cm. Shape: Narrowly ovate with pointed lobes. Apex: Elongated acuminate. Base: Rounded acute. Margin: Entire. Texture: Smooth, slightly rugose. Aspect: Somewhat erect. Color: Developing, upper surface: Much darker and more crimson than 53A. Developing, lower surface: 53B. Mature, upper surface: Slightly darker than 45B. Mature, lower surface: 53B.

*Cyathia*.—Quantity: Usually about 10 per corymb. Diameter of cyathia cluster: About 8 by 10 mm. Length: About 7 mm. Width: About 4 mm. Color: Immature: 144A. Mature: 144A. Peduncle: Length: About 2 mm. Aspect: Strong, erect. Color: 144A. Stamens: Stamen number: Typically about 5 to 10 with numerous stamenoids per cyathium. Anther size: Less than 1 mm. Anther shape: Oval. Amount of pollen: Scarce. Pistils: No pistillate flowers observed. Nectary color: 14A.

Disease resistance: Plants of the new Poinsettia have been observed to be resistant to Botrytis.

Postproduction longevity: Excellent; plants of the new Poinsettia maintain good substance and bract color for about eight weeks under interior conditions.

It is claimed:

1. A new and distinct cultivar of Poinsettia plant named 'Jacabia', as illustrated and described.

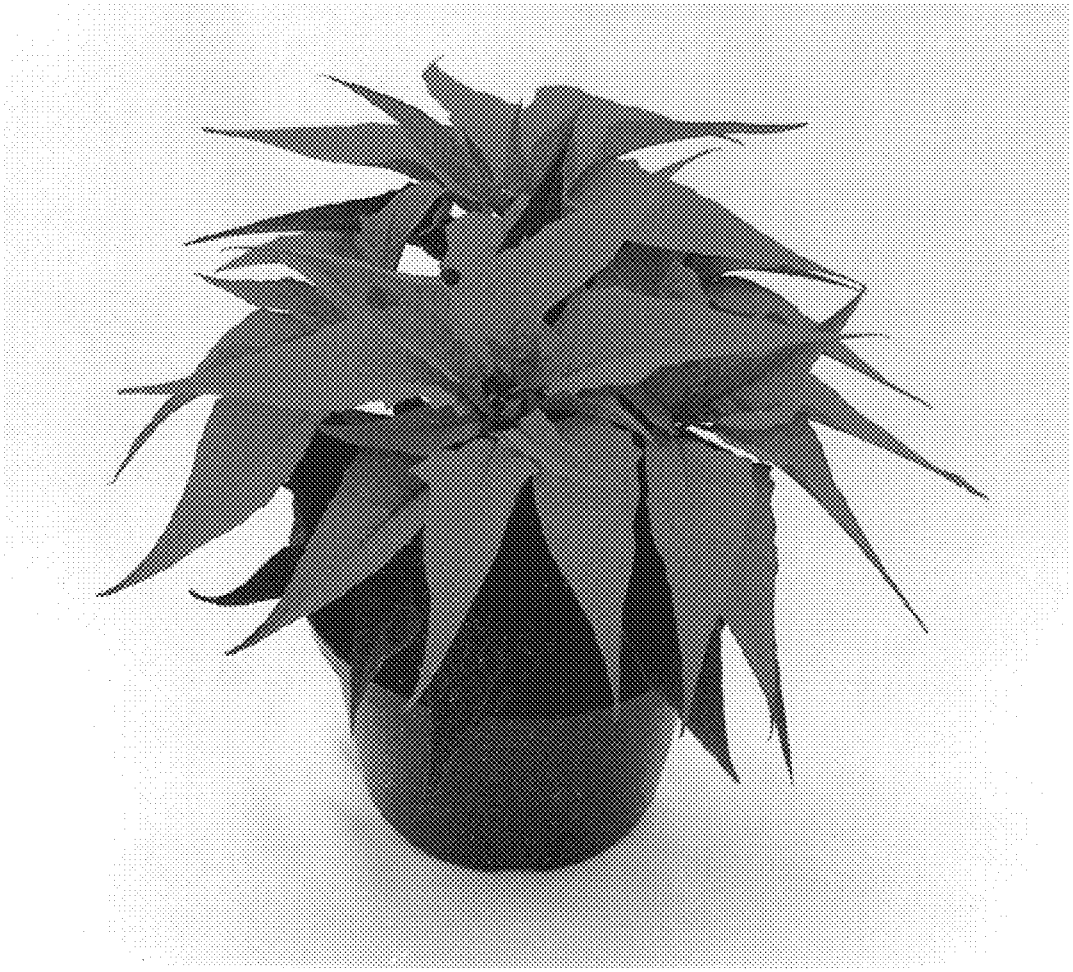
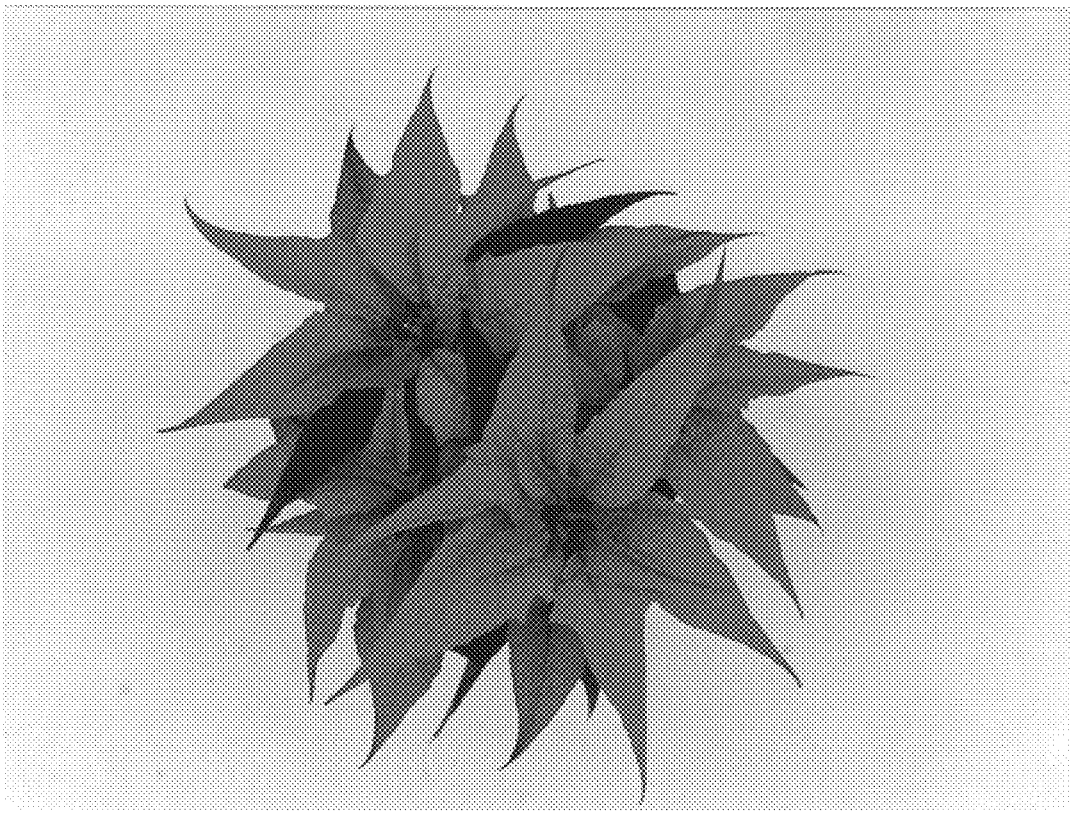

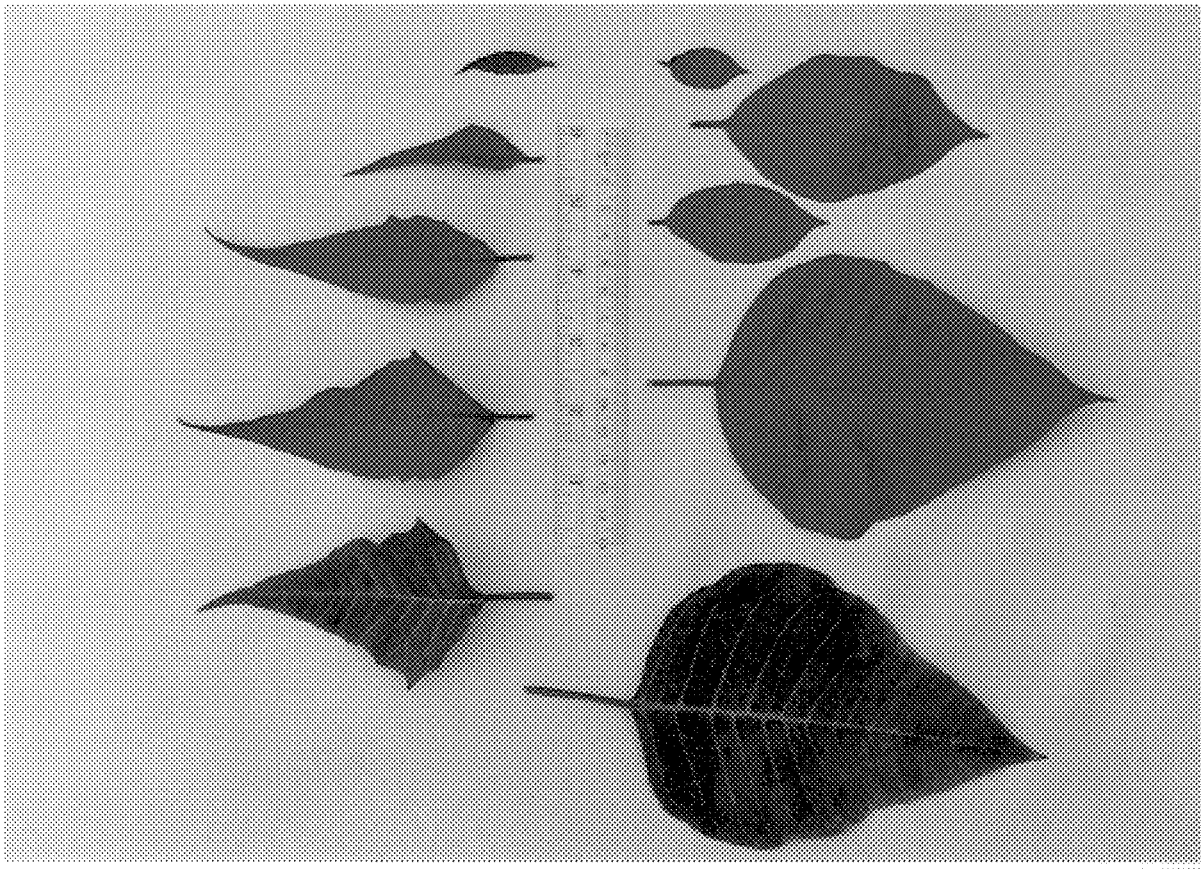

* * * * *